(12) United States Patent
Talaber et al.

(10) Patent No.: US 6,261,291 B1
(45) Date of Patent: *Jul. 17, 2001

(54) ORTHOPEDIC IMPLANT ASSEMBLY

(76) Inventors: David J. Talaber, 5185 Charlotte Way, Livermore, CA (US) 94550-3532; James R. Lloyd, 1080 Circle Dr., Elm Grove, WI (US) 53122

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/349,519

(22) Filed: Jul. 8, 1999

(51) Int. Cl.$^7$ .................................................. A61B 17/70
(52) U.S. Cl. ................................ 606/69; 606/71; 606/73
(58) Field of Search .................................. 606/60, 63, 66, 606/68, 70, 71, 72, 73, 86

(56) References Cited

U.S. PATENT DOCUMENTS

| | | |
|---|---|---|
| 3,350,103 | 10/1967 | Ahlstone . |
| 3,863,959 | 2/1975 | Blaschke . |
| 4,017,946 | 4/1977 | Soja . |
| 4,280,742 | 7/1981 | Justman . |
| 4,488,543 * | 12/1984 | Tornier .................................. 606/66 |
| 4,662,461 | 5/1987 | Garrett . |
| 4,696,290 | 9/1987 | Steffee . |
| 5,054,347 | 10/1991 | Johnson et al. . |
| 5,169,597 | 12/1992 | Davidson et al. . |
| 5,275,601 | 1/1994 | Gogolewski et al. . |
| 5,364,399 | 11/1994 | Lowery et al. . |
| 5,372,660 | 12/1994 | Davidson et al. . |
| 5,509,933 | 4/1996 | Davidson et al. . |
| 5,520,690 | 5/1996 | Errico et al. . |
| 5,534,032 | 7/1996 | Hodorek . |
| 5,569,251 | 10/1996 | Baker et al. . |
| 5,578,034 | 11/1996 | Estes . |
| 5,601,553 | 2/1997 | Trebing et al. . |
| 5,607,426 | 3/1997 | Ralph et al. . |
| 5,643,265 | 7/1997 | Errico et al. . |
| 5,725,588 | 3/1998 | Errico et al. . |
| 5,735,853 | 4/1998 | Olerud . |
| 5,785,711 | 7/1998 | Errico et al. . |
| 5,807,396 | 9/1998 | Ravch . |
| 5,810,819 | 9/1998 | Errico et al. . |
| 5,843,082 | 12/1998 | Yuan et al. . |

(List continued on next page.)

FOREIGN PATENT DOCUMENTS

| | | |
|---|---|---|
| 4409833 A1 | 10/1995 | (DE) . |
| 19545612 A1 | 6/1997 | (DE) . |
| WO 98/17188 | 4/1998 | (WO) . |
| WO 98/48739 | 11/1998 | (WO) . |
| WO 99/09904 | 3/1999 | (WO) . |

Primary Examiner—Michael Buiz
Assistant Examiner—William Lewis
(74) Attorney, Agent, or Firm—Heller Ehrman White & McAuliffe LLP

(57) ABSTRACT

An orthopedic implant assembly comprising a stabilizing element, a securing element which attaches the stabilizing element to the bone, and a stopping member in the stabilizing element which inhibits the securing element from loosening or backing out of the bone. The stabilizing element has at least one bore with the stopping member therein. In one embodiment, the stopping member has a reversibly expandable inner and outer diameter to allow the securing element to pass posteriorly through the stopping member, but thereafter prevent or inhibit the securing element from anteriorly backing out of the posterior section of the transverse passageway. In another embodiment, the stopping member is secured to an anterior section of the transverse passageway, and the head of the securing element generally has a compressed configuration with a diameter less than the diameter of the stopping member, in which configuration the head can pass through the stopping member, and an uncompressed configuration with a diameter larger than the diameter of the stopping member.

28 Claims, 7 Drawing Sheets

U.S. PATENT DOCUMENTS

| | | |
|---|---|---|
| 5,876,402 | 3/1999 | Errico et al. . |
| 5,879,389 | 3/1999 | Koshino . |
| 5,904,683 * | 5/1999 | Pohndorf .............................. 606/69 |
| 5,928,243 | 7/1999 | Guyer . |
| 5,935,133 | 8/1999 | Wagner et al. . |
| 5,961,518 | 10/1999 | Errico et al. . |
| 5,964,769 | 10/1999 | Wagner et al. . |
| 5,989,250 | 11/1999 | Wagner et al. . |
| 5,997,539 | 12/1999 | Errico et al. . |
| 6,017,344 | 1/2000 | Errico et al. . |
| 6,030,389 | 2/2000 | Wagner et al. . |
| 6,045,579 | 4/2000 | Hochshuler et al. . |
| 6,053,921 | 4/2000 | Wagner et al. . |
| 6,117,173 | 9/2000 | Taddia et al. . |

* cited by examiner

ORTHOPEDIC IMPLANT ASSEMBLY

BACKGROUND OF THE INVENTION

This invention generally relates to the field of medical devices, and particularly to an orthopedic implant for joining bone segments and methods of use thereof.

A variety of medical conditions may necessitate the joining of bone segments together, as for example, in the treatment of broken bones, spinal disorders, or the fusion of vertebrae following the removal of a spinal disk. Orthopedic implants used to join bone segments include rods, plates, and screws. In the case of rods and plates, the implants have been attached to the bone using a variety of methods including cementing and screwing the implant to the bone. The bone is typically drilled out to receive the screw therein, or to receive an anchor having a hollow shank which fixedly receives the screw therein. However, one disadvantage has been the tendency of the implants to loosen or detach from the bone over time.

It would be a significant advance to provide an orthopedic implant for joining bone segments together which durably and securely attaches to the bone.

SUMMARY OF THE INVENTION

This invention is directed to an orthopedic implant assembly generally comprising a stabilizing element, a securing element which attaches the stabilizing element to the patient's bone, and a stopping member in the stabilizing element which defines at least in part a passageway and which inhibits or prevents the securing element from loosening or backing out of the bone.

The stabilizing element is generally a plate or rod, which has at least one bore therein having a first opening in the anterior surface of the stabilizing element, a second opening in the posterior surface of the stabilizing element, and a transverse passageway extending from the first opening to the second opening. The term posterior should be understood to mean an inner portion of the assembly closer to the bone to which the assembly is attached, and the term anterior should be understood to mean an outer portion of the assembly farther away from the bone.

In one embodiment, the stopping member defines a reversibly expandable passageway, and is biased to the unexpanded, or smaller diameter, passageway configuration. In one embodiment, the biased stopping member comprises an annular collar having a reversibly expandable inner diameter. The biased stopping member may be configured to be positioned in a groove in the transverse passageway after the securing element is in place in the transverse passageway of the stabilizing element. Alternatively, in a presently preferred embodiment, the biased stopping member is configured to allow the securing element to pass posteriorly through the stopping member passageway from the anterior surface of the stabilizing element into a posterior section of the transverse passageway. In another embodiment, the biased stopping member is secured to the stabilizing element within the transverse passageway, and is deflectable. The deflectable stopping member reversibly flexes as the head of the securing element is posteriorly displaced through the deflectable stopping member to expand the passageway defined by the stopping member. The deflectable stopping member is biased to the undeflected or smaller diameter passageway configuration. The stopping member prevents the securing element from anteriorly backing out of the posterior section of the transverse passageway. As a result, the securing element durably attaches the stabilizing element to the bone.

The securing element is configured to attach to bone, and generally comprises an elongated body and a head at one end of the body and integral therewith. The term integral should be understood to mean the securing element is a one-piece unit, with the head secured to the body so that there is no relative movement between the head and the body. In one embodiment, the securing element is selected from the group consisting of screws, pins, and nails. In a presently preferred embodiment where the collar is seated within the groove in the stabilizing element before the securing element is advanced therein, the head of the securing element has a shaped posterior surface which contacts the collar and gradually expands the collar as the head is displaced into the posterior section of the transverse passageway of the stabilizing element. In a presently preferred embodiment, the head of the securing element has a curved posterior surface. However, other suitable shapes may be used including tapered posterior surfaces.

The invention also includes methods of attaching an orthopedic implant assembly to a bone of a patient. The bone is typically prepared for receiving the body of the securing element, as for example by drilling a cavity into the bone, and/or tapping the cavity. A method generally comprises positioning the posterior surface of the stabilizing element against the surface of the bone, with the stopping member within the groove of the stabilizing element in the unexpanded configuration, introducing the body of the securing element into the transverse passageway, posteriorly displacing the head of the securing element through the stopping member and thereby expanding the stopping member, and attaching the stabilizing element to the bone by advancing the head of the securing element posteriorly of the stopping member so that the stopping member contracts and returns to a smaller transverse, i.e., unexpanded diameter, configuration. The head of the securing element is positioned within a posterior section of the transverse passageway between the stopping member and the second opening in the stabilizing element, and the body of the securing element is positioned within the patient's bone. In an alternative embodiment, the stopping member may be placed within the groove after the head of the securing element is positioned within the posterior section of the transverse passageway. The stabilizing element is attached to the bone by the securing element, which is attached to the bone and retained within the transverse passageway.

In another embodiment of the invention, the head of the securing element can be reversibly compressed, and the stopping member is secured to an anterior section of the transverse passageway. The stopping member defines a passageway with a fixed diameter, but the compressed configuration of the head of the securing element has a diameter less than the diameter of the stopping member so that the head can pass through the stopping member passageway. In the uncompressed configuration, the head of the securing element has a diameter larger than the diameter of the stopping member and the diameter of the second opening in the stabilizing element, so that the head can be advanced posteriorly of the stopping member and retained within the transverse passageway between the stopping member and the second opening.

To facilitate the correct placement of the orthopedic implant assembly on the bone, the transverse passageway between the collar and the second opening in the stabilizing element may be configured so that the securing element may be angularly displaceable therein and the body of the securing element may be positioned at an angle within the patient's bone.

In the assembly of the invention, the securing element is prevented from backing out of the bone by the interaction of the securing element head and the stopping member. As a result, a separate anchor means implanted in the bone to receive the screw is not required, and the resulting loss of bone and intraoperative time required to implant the anchor is avoided. Moreover, in a preferred embodiment, the stopping member is within the transverse passageway at the beginning of the procedure, so that the surgeon can attach the implant assembly to the bone with the single motion of advancing the securing element through the stopping member passageway and into the bone. The implant assembly of the invention thus reduces the time required to attach the assembly to the bone and provides improved implant performance.

The orthopedic implant assembly of the invention can be durably attached to bone, and the securing element prevented from significantly backing out of the bone due to the head of the securing element being retained within the stabilizing element. These and other advantages of the invention will become more apparent from the following detailed description of the invention and the accompanying exemplary drawings.

DETAILED DESCRIPTION OF THE INVENTION

Figure 1:
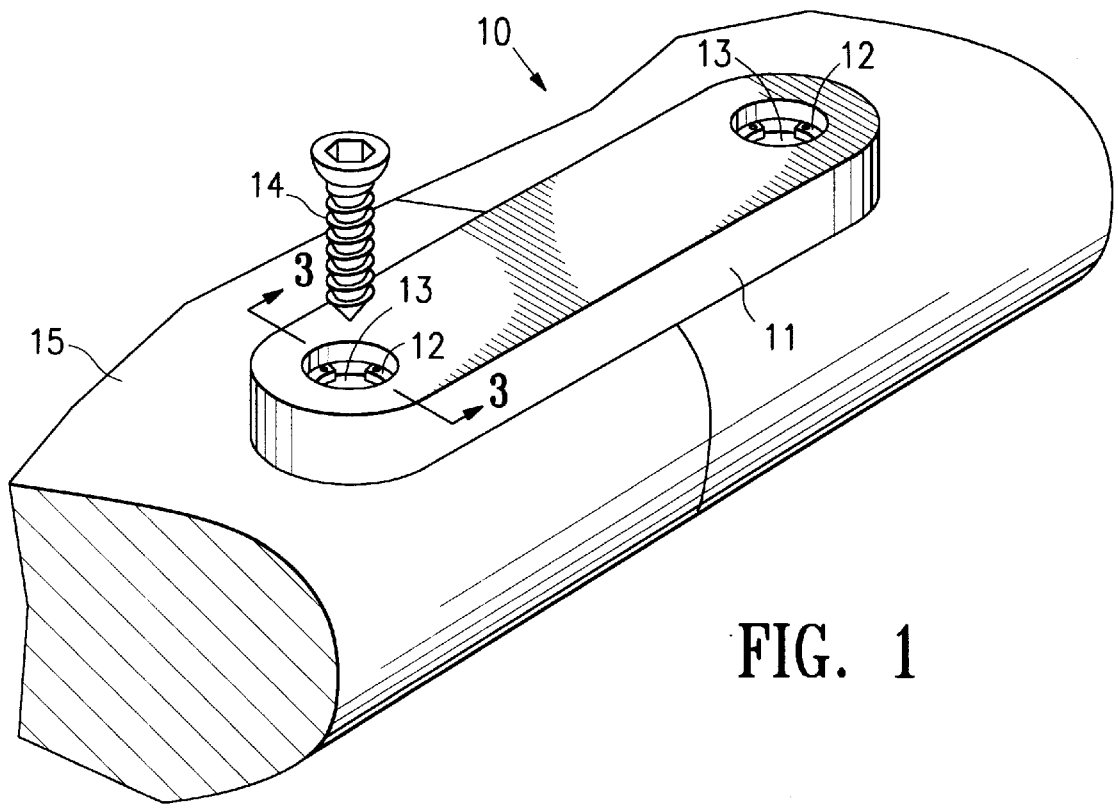
FIG. 1 is an elevational view of an orthopedic implant assembly which embodies features of the invention.

FIG. 1 illustrates one embodiment of the orthopedic implant assembly 10 of the invention, generally including a stabilizing element 11, with a biased stopping member 12 in a bore 13 therein, and a securing element 14, configured for securing to a patient's bone 15. In the embodiment illustrated in FIG. 1, the biased stopping member comprises an annular collar, although a variety of suitable members may be used, as for example, one or more contractible fingers biased to extend into the transverse passageway (not shown).

Figure 2:
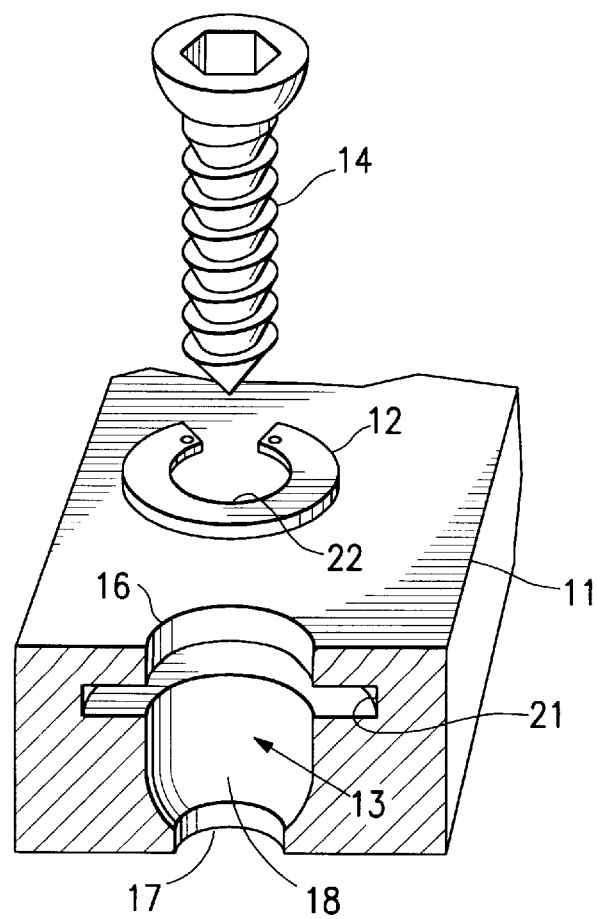
FIG. 2 is an exploded view, partially in section, of the orthopedic implant assembly shown in FIG. 1.
Figure 3:
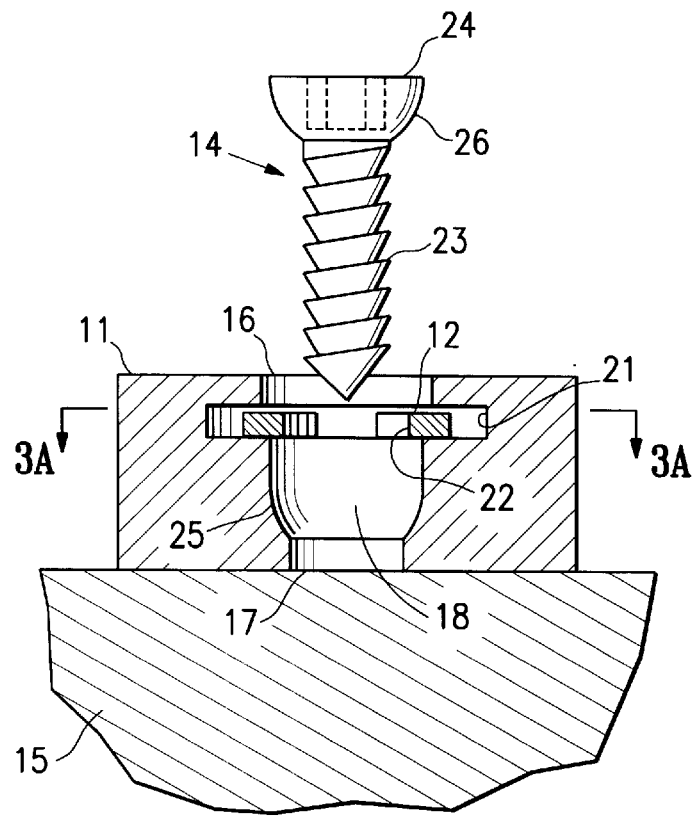
FIG. 3 is a cross section of the orthopedic implant assembly shown in FIG. 1 taken along lines 3—3.
Figure 3A:
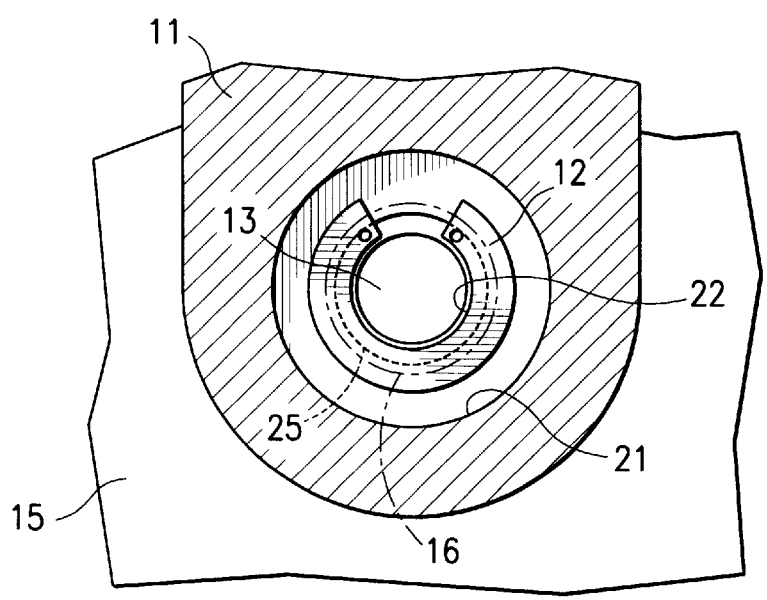
FIG. 3A is a transverse cross section of the orthopedic implant assembly shown in FIG. 3 taken along lines 3A—3A.

As best illustrated in FIG. 2 showing an exploded, partially in section, view of the assembly shown in FIG. 1, the bore 13 of the stabilizing element has a first opening 16 in an anterior surface of the stabilizing element, a second opening 17 in a posterior surface of the stabilizing element, a transverse passageway 18 extending therein, and a groove 21 in an anterior portion of the transverse passageway. Annular collar 12 defines a passageway 22, and is configured to be seated within the groove 21, and has a reversibly expandable inner and outer diameter. As illustrated in FIG. 3, illustrating the assembly shown in FIG. 1 partially in section taken along lines 3—3, and FIG. 3A illustrating a transverse cross sectional view of the assembly shown in FIG. 3 taken along lines 3A—3A, the annular collar 12 is biased to an unexpanded outer diameter which is less than the diameter of the groove and greater than the diameter of the transverse passageway, so that the collar seats within the groove. The expanded outer diameter of the collar is less than the diameter of the groove, and the height of the collar is less than the height of the groove, so that the collar can be expanded therein.

The securing element 14 has an elongated body 23 and an integral head 24 secured to one end of the body 23. In a presently preferred embodiment of the invention illustrated in FIG. 1, the securing element comprises a screw. The head of the securing element is configured to be posteriorly displaceable through the passageway 22 of the collar seated within the groove, from an anterior to a posterior surface of the collar, and retained within a posterior section 25 of the transverse passageway 18 between the posterior surface of the collar 12 and the second, i.e., posterior, opening 17 in the stabilizing element. In the embodiment illustrated in FIG. 1, the head of the securing element has a curved posterior surface 26 with a convex shape and with a smaller diameter than an anterior surface of the head. The curved posterior surface 26 has a minimum outer diameter which is smaller than the unexpanded inner diameter of the collar, and which is positionable within the passageway of the collar, to contact and expand the collar as the head is displaced posteriorly therein.

Figure 4:
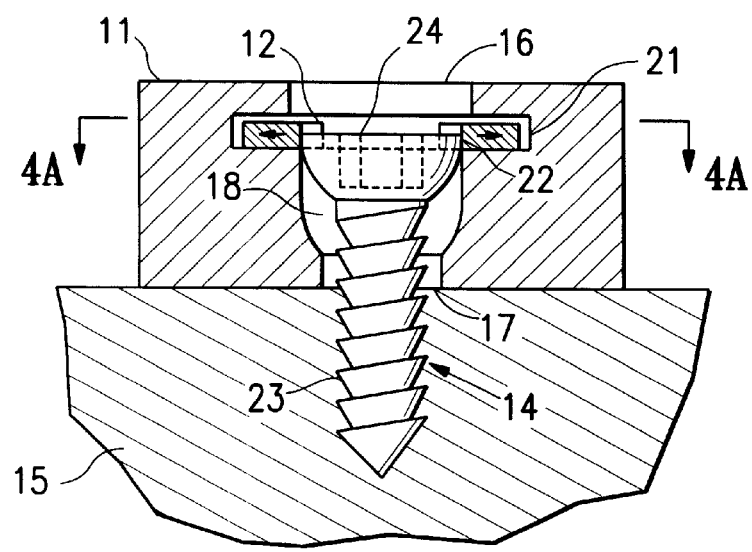
FIG. 4 illustrates the orthopedic implant assembly shown in FIG. 3, as the securing element is being advanced into the patient's bone.
Figure 4A:
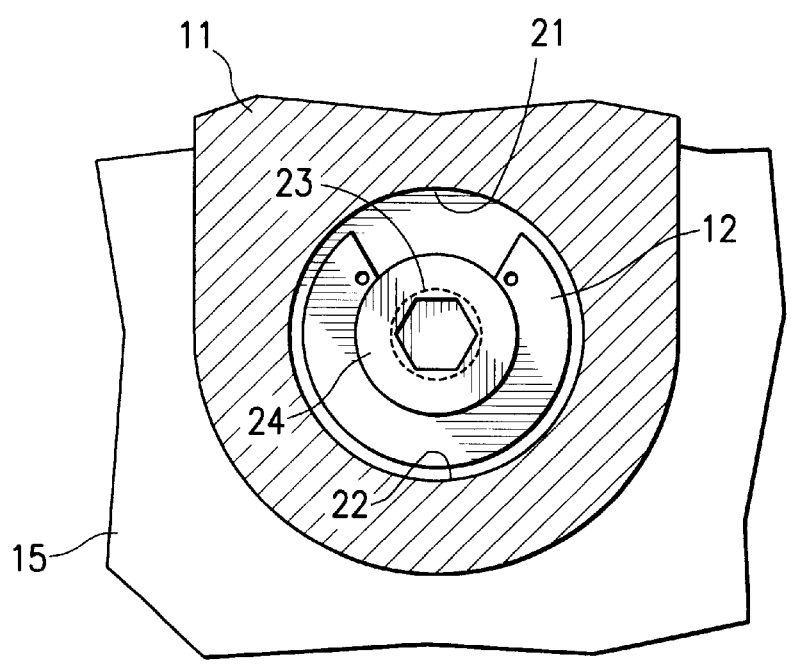
FIG. 4A is a transverse cross section of the assembly shown in FIG. 4, taken along lines 4A—4A.
Figure 5:
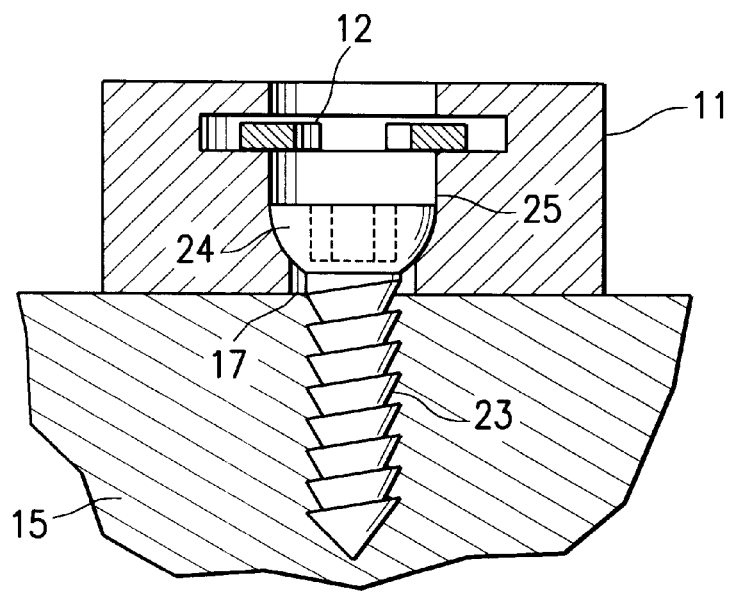
FIG. 5 illustrates the orthopedic implant assembly shown in FIG. 3, with the securing element advanced into the posterior section of the transverse passageway of the stabilizing element.

FIGS. 3–5 illustrate the attachment of the assembly to the patient's bone. As illustrated in FIG. 3, the stabilizing element is positioned against a surface of a bone 15, and the posterior end of the body of the securing element 14 is placed within the stabilizing element transverse passageway. The head 24 of the securing element is posteriorly advanced within the passageway 22 of the collar 12, thereby applying a radially expanding force against an inner surface of the collar to expand the inner diameter of the collar, as illustrated in FIG. 4 showing the expanded collar and the head of the securing element partially displaced through the collar passageway. Arrows in FIG. 4 illustrate the expansion of the collar as the head of the securing element is passed therethrough. FIG. 4A illustrates a transverse cross section of the assembly shown in FIG. 4, taken along lines 4A—4A. The expanded inner diameter of the collar is therefore larger than the maximum diameter of the head of the securing element, to allow the head of the securing element to pass posteriorly through the collar. The head of the securing element is advanced posteriorly of the collar and into the posterior section 25 of the transverse passageway, so that the collar returns to the unexpanded configuration having an unexpanded inner diameter smaller than the maximum diameter of the head of the securing element, as illustrated in FIG. 5. In the embodiment illustrated in FIG. 5, the flat anterior surface of the head of the securing element has a diameter which is larger than the unexpanded inner diameter of the collar, and the posterior surface of the collar is perpendicular to the longitudinal axis of the transverse passageway. Thus, the anterior surface of the head will butt up against the posterior surface of the collar without expanding the collar, to prevent the securing element from being anteriorly displaced out of the posterior section of the transverse passageway. In the embodiment illustrated in the FIG. 5, a posterior portion of the transverse passageway is curved to conform to the curved posterior surface of the head, providing maximum contact between the securing element and the stabilizing element. The curved surfaces of the posterior portion of the transverse passageway and the posterior surface of the head have the same radius of curvature, and the diameter of the curved surface of the head is large enough so that the wall defining the transverse passageway contacts the head around the circumference of the curved posterior surface of the head, but is small enough so that the head can be displaced within the transverse passageway. With the head of the securing element positioned within the posterior section 25 of the transverse passageway, the body of the securing element is embedded in, and secured to, the bone of the patient.

Figure 6:
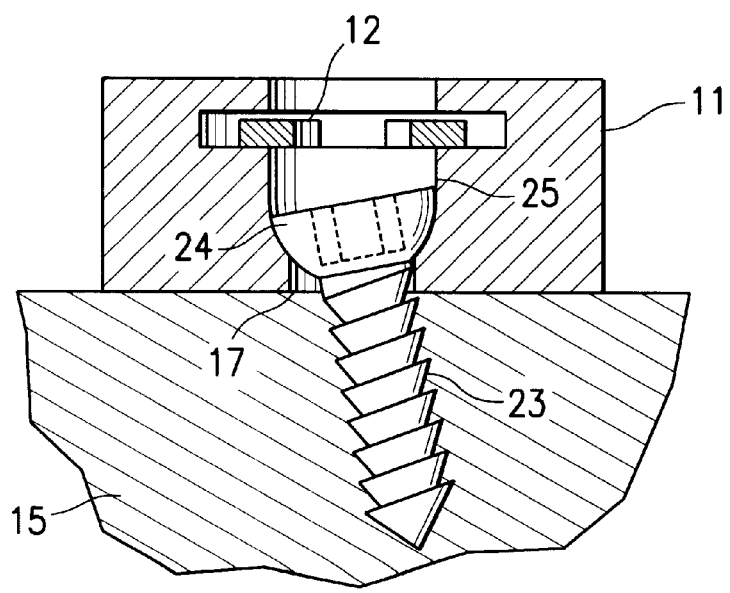
FIG. 6 illustrates the orthopedic implant assembly shown in FIG. 3, with the securing element angularly disposed within the patient's bone.
Figure 7:
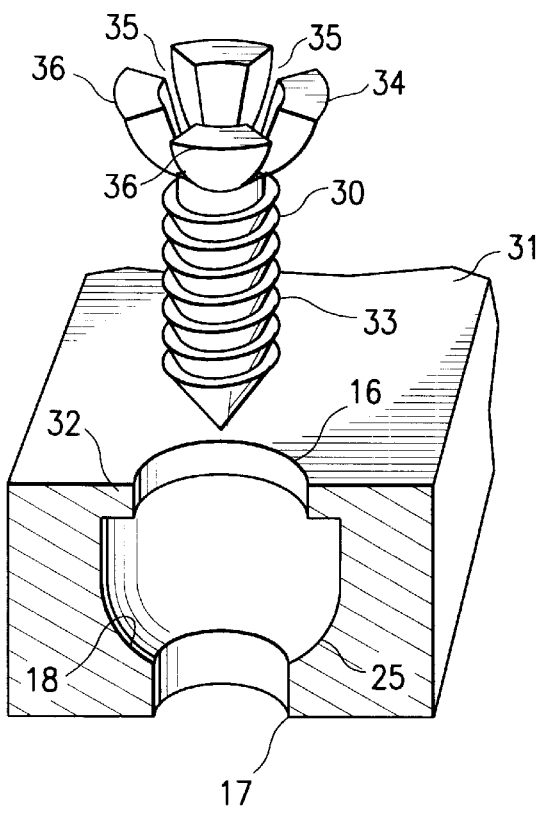
FIG. 7 is an exploded view, partially in section, of an orthopedic implant assembly having a securing element with a compressible head, which embodies features of the invention.

In the embodiment illustrated in FIG. 5, the posterior section 25 of the transverse passageway is sufficiently longer than the head 24 of the securing element so that the head can be displaced anteriorly and posteriorly, and is thus longitudinally displaceable within the posterior section of the transverse passageway. Additionally, the body of the securing element 23 has a smaller diameter than the diameter of the second opening 17 in the stabilizing element, and can be displaced from side to side, i.e., medial-lateral displacement, within the second opening 17. As a result, the securing element is angularly displaceable within the transverse passageway posterior section 25 between the collar 12 and the second opening 17 in the stabilizing element, as illustrated in FIG. 6. The securing element can thus be tilted within the transverse passageway at an angle relative to the transverse passageway longitudinal axis, to facilitate positioning the securing element at a desired location in the bone by advancing the body of the securing element within the bone at an angle relative to the surface of the bone. The securing element can be angularly displaced up to an angle of about 45°, preferably up to about 20° relative the longitudinal axis of the transverse passageway.

The stopping member 12 is preferably elastically deformable, and formed of titanium, and superelastic or pseudoelastic materials such as NiTi alloys. The unexpanded inner diameter of the stopping member is about 0.1 to about 40 mm, preferably about 0.5 to about 20 mm, and is about 0.05 to about 20 mm, preferably about 0.1 to about 15 mm less than the maximum transverse dimension of the head of the securing element. The unexpanded outer diameter of the stopping member is about 0.2 to about 50 mm, preferably about 1.0 to about 30 mm. The expanded inner diameter of the stopping member is about 0.15 to about 50 mm, preferably about 0.75 to about 30 mm, and the expanded outer diameter of the stopping member is about 0.5 to about 60 mm, preferably about 1.5 to about 40 mm. The height of the stopping member is about 0.01 to about 5 mm, preferably about 0.05 to about 3 mm.

Figure 9:
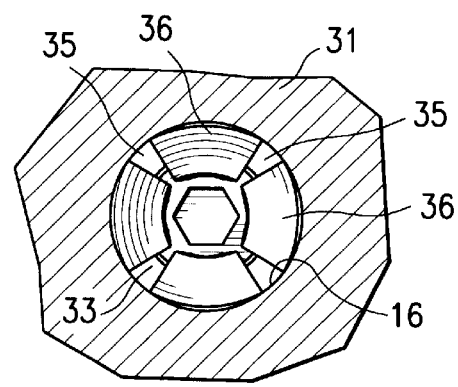
FIGS. 9 is a transverse cross section of the assembly shown in FIG. 8, taken along lines 9—9.
Figure 8:
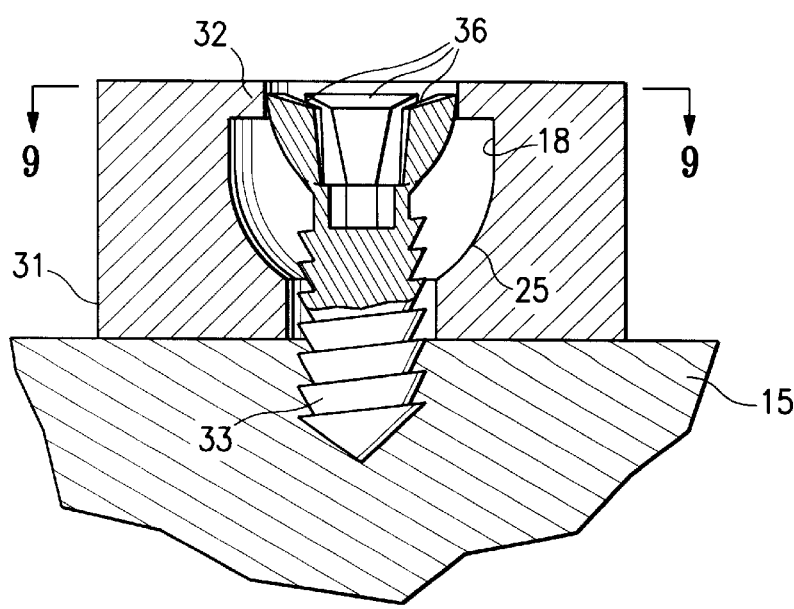
FIG. 8 illustrates the orthopedic implant assembly shown in FIG. 7 as the securing element is being advanced into the patient's bone.
Figure 10:
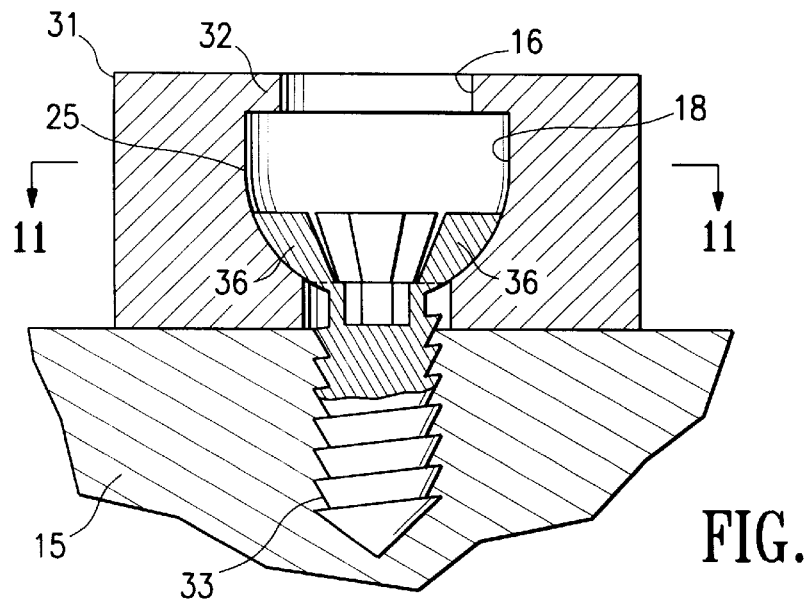
FIG. 10 illustrates the orthopedic implant assembly shown in FIG. 7 with the securing element advanced into the posterior section of the transverse passageway of the stabilizing element.
Figure 11:
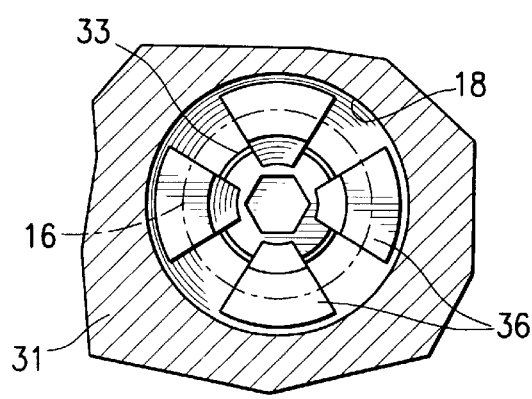
FIG. 11 is a transverse cross section of the assembly shown in FIG. 10, taken along lines 11—11.
Figure 12:
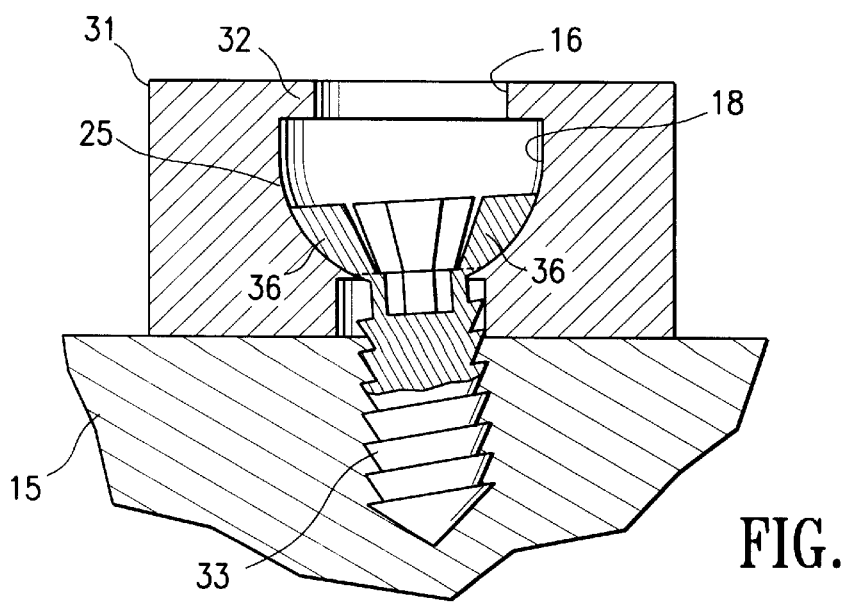
FIG. 12 illustrates the orthopedic implant assembly shown in FIG. 7, with the securing element angularly disposed within the patient's bone.

FIGS. 7–12 illustrate another embodiment of the invention, generally comprising a securing element 30, and a stabilizing element 31 similar to the stabilizing element in the embodiment illustrated in FIG. 1, except the stopping member is not seated within a groove in the transverse passageway 18. Instead, a stopping member 32 is provided at an anterior section of the transverse passageway, which may be formed integrally with the stabilizing element or as a separate member secured thereto. In the embodiment illustrated in FIG. 7, the stopping member is a collar at the anterior end of the transverse passageway and defining the first opening 16 in the stabilizing element 31. The securing element 30 has an elongated body 33, and head 34 secured to one end of the body having a compressed configuration and an uncompressed configuration. In the embodiment illustrated in FIG. 7, the head has a plurality of slots 35 defining circumferentially spaced members 36 having posterior ends secured to the body of the securing element. The circumferentially spaced members 36 have anterior ends radially moveable toward a longitudinal axis of the head to form the compressed configuration, having a diameter less than the inner diameter of the collar. FIG. 8 illustrates the head of the securing element in the compressed configuration within the passageway defined by the collar. FIG. 9 illustrates a transverse cross sectional view of the assembly shown in FIG. 8, taken along lines 9—9. FIG. 10 illustrates the head of the securing element advanced posteriorly of the collar and into the posterior section of the transverse passageway, thereby returning the circumferentially spaced members 36 to the uncompressed configuration by release of the radially compressive force of the collar. FIG. 11 illustrates a transverse cross section of the assembly shown in FIG. 10, taken along lines 11—11, with the first opening 16 shown in phantom. The securing element is angularly and longitudinally displaceable within the transverse passageway posterior section 25, as discussed above with regard to the embodiment illustrated in FIG. 1, and as illustrated in FIG. 12.

Figure 13:
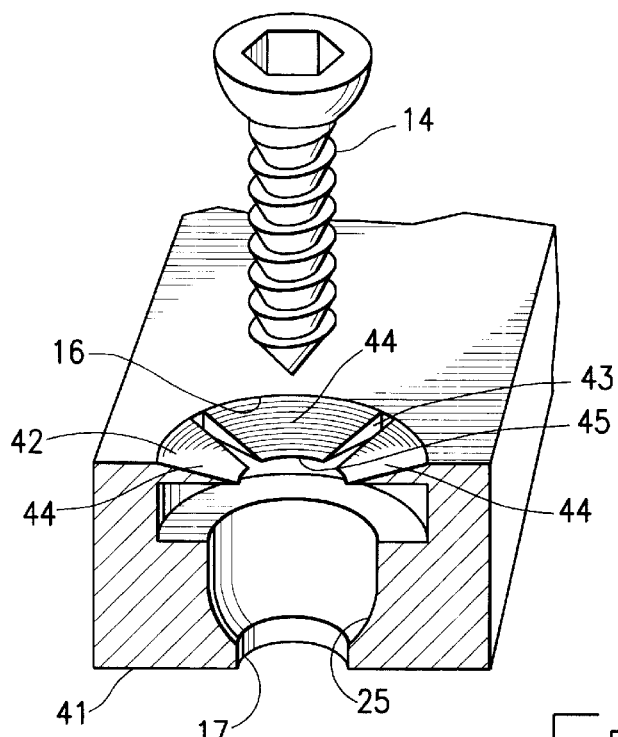
FIG. 13 is an exploded view, partially in section, of an orthopedic implant assembly having a deflectable stopping member, which embodies features of the invention.
Figure 14:
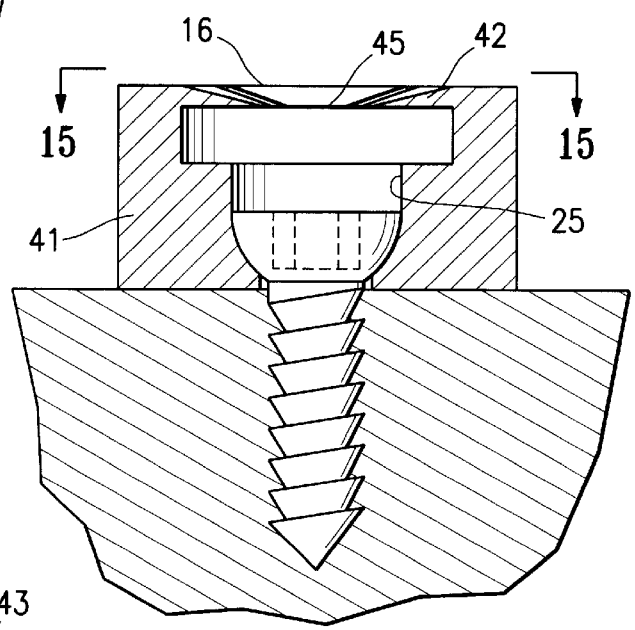
FIG. 14 illustrates the orthopedic implant assembly shown in FIG. 13 with the securing element advanced into the posterior section of the transverse passageway of the stabilizing element.
Figure 15:
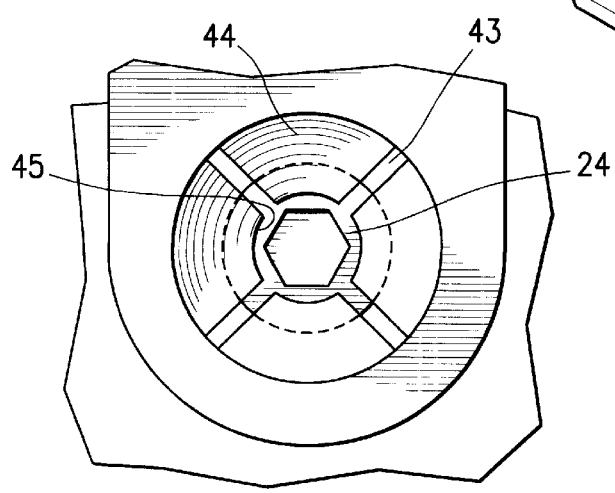
FIGS. 15 is a plan view of the assembly shown in FIG. 14, taken along lines 15—15.

FIGS. 13–15 illustrate another embodiment of the invention, generally comprising a stabilizing element 41 similar to the stabilizing element in the embodiment illustrated in FIG. 1, except with a deflectable stopping member 42 provided in an anterior section of the transverse passageway, which may be formed integrally with the stabilizing element or as a separate member secured thereto. In the embodiment illustrated in FIG. 13, the stopping member comprises a collar 42 having a plurality of slots 43 defining circumferentially spaced members 44 and a tapered or sloping anterior surface providing axial flexibility in a posterior direction, so that the collar deflects posteriorly when the head of the securing element is posteriorly displaced through the collar. As a result, the circumferentially spaced members 44 have a wedge shape and a height which tapers towards the central passageway 45 defined by the collar, which facilitates displacing the head of the securing element therethrough and reversibly enlarging the passageway 45. In the embodiment illustrated in FIG. 13, the collar is integrally formed with the stabilizing element 41 at the anterior end of the transverse passageway, and defines the first opening 16 in the stabilizing element 41. The securing element may be the same as, or similar to, the securing element 14 discussed above in connection with the embodiment illustrated in FIG. 1, and as illustrated in FIG. 13. However, securing element 30 having head 34 with a compressed configuration and an uncompressed configuration, as discussed above in connection with the embodiment illustrated in FIG. 7, may also be used. FIG. 15 illustrates a plan view of the assembly shown in FIG. 14, taken along lines 15—15, with the head of the securing element 14 partially in phantom. The angular and longitudinal displacement of the securing member in the posterior section 25 of the transverse passageway is as discussed above.

The stabilizing element is preferably formed of a metal such as titanium or stainless steel. The length of the stabilizing element is typically about 7 to about 300 mm, preferably about 13 to about 200 mm, and the width of the stabilizing element is typically about 5 to about 50 mm, preferably about 10 to about 30 mm. The height of the stabilizing element is typically about 0.5 to about 10 mm, preferably about 1.0 to about 6.0 mm although the dimensions of the stabilizing element will vary depending on the application for which the assembly is to be used.

The securing element is preferably formed of a metal, such as titanium or stainless steel. The head of the securing element is configured, as for example with a hexagonal opening, for releasable connection to a tool for advancing the securing element into the bone. The body of the securing element has a length of about 2 to about 50 mm, preferably about 5 to about 20 mm, and the head of the securing element has a length of about 0.05 to about 1.5 mm, preferably about 0.5 to about 1.0 mm. One skilled in the art will recognize that a variety of suitable securing elements may be used, which may be optimized for use in a particular orthopedic environment, as is well known in the art. For example, a high thread pitch may be used to limit screw back out from bone.

The assembly of the invention is suitable for use in a variety of medical procedures, including securing fractured bone segments or vertebrae following disk removal. In the illustrated embodiments, the stabilizing element comprises a plate, although other suitable elements such as rods may be used. Additionally, the stabilizing element may be shaped to conform to the surface of the bone or bones to which it will be attached. For example, a presently preferred embodiment of the stabilizing element comprises a plate with a concave posterior surface, and is configured for attaching to vertebrae.

While the present invention has been described herein in terms of certain preferred embodiments, those skilled in the art will recognize that modifications and improvements may be made without departing from the scope of the invention. For example, while the stopping member is discussed primarily in terms of a collar, other configurations may also be used. Additionally, while a particular feature may be discussed in connection with one embodiment, it should be understood that features of one embodiment may be used with the other embodiments herein.

What is claimed is:

1. An orthopedic implant assembly, comprising
   a) a stabilizing element having an anterior surface, a posterior surface, and at least one bore, the bore having a first opening in the anterior surface, a second opening in the posterior surface smaller than the first opening, and a transverse passageway extending from the first opening to the second opening;
   b) a biased stopping member defining at least in part a reversibly expandable passageway having a smaller diameter configuration and a larger diameter configuration; and
   c) a securing element having an elongated body, and a head at one end of the body and integral therewith, the head having a maximum diameter greater than the smaller diameter configuration of the passageway defined by the biased stopping member and greater than the second opening in the stabilizing element, so that the head is retained within the transverse passageway between the biased stopping member and the second opening in the stabilizing element.

2. The assembly of claim 1 wherein the biased stopping member comprises a collar defining a passageway, enlargeable from an unexpanded inner diameter to an expanded inner diameter, wherein the head of the securing element has a maximum diameter greater than the unexpanded inner diameter of the collar and less than the expanded inner diameter of the collar.

3. The assembly of claim 2 wherein the head of the securing element has a curved posterior surface which has a minimum outer diameter smaller than the unexpanded inner diameter of the collar, configured to be displaceable posteriorly of the collar through the passageway of the collar from an anterior to a posterior surface thereof.

4. The assembly of claim 2 wherein the bore has a groove in an anterior portion of the transverse passageway having a diameter and a height, and wherein the collar is a reversibly expandable annular collar seated in the groove, the collar having an expanded outer diameter, and an unexpanded outer diameter which is less than the diameter of the groove and greater than a diameter of the transverse passageway.

5. The assembly of claim 4 wherein the head of the securing element has a curved posterior surface which has a minimum outer diameter smaller than the unexpanded inner diameter of the collar, and which is configured to contact the collar anterior surface and expand the collar as the head is displaced posteriorly through the collar passageway.

6. The assembly of claim 2 wherein the collar is secured to an anterior section of the transverse passageway, and has a plurality of slots and circumferentially spaced members, the circumferentially spaced members having a deflected configuration defining the expanded inner diameter of the collar.

7. The assembly of claim 6 wherein the head of the securing element has a curved posterior surface which has a minimum outer diameter smaller than the unexpanded inner diameter of the collar, and which is configured to contact the collar anterior surface and deflect the circumferentially spaced members away from a longitudinal axis of the transverse passageway as the head is displaced posteriorly through the collar passageway.

8. The assembly of claim 6 wherein the collar has an anterior surface which tapers toward a center of the transverse passageway.

9. The assembly of claim 3 wherein a posterior portion of the transverse passageway is curved to conform to the curved posterior surface of the head.

10. The assembly of claim 1 wherein the head of the securing element is longitudinally displaceable within the transverse passageway between a posterior surface of the biased stopping member and the second opening in the posterior surface of the stabilizing element.

11. The assembly of claim 10 wherein the body of the securing element has a diameter smaller than the second opening in the stabilizing element, and the securing element may be angularly displaced within the transverse passageway and the second opening in the stabilizing element.

12. The assembly of claim 1 wherein the stabilizing element includes at least two bores.

13. The assembly of claim 1 wherein the stabilizing element is configured to conform to and extend between at least two bone segments.

14. The assembly of claim 13 wherein the stabilizing element has a curved surface.

15. The assembly of claim 1 wherein the stabilizing element is selected from the group consisting of rods and plates.

16. The assembly of claim 1 wherein the securing element is selected from the group consisting of screws and nails.

17. The assembly of claim 2 wherein the collar is formed of an elastically deformable material.

18. The assembly of claim 2 wherein the collar is formed of a material selected from the group consisting of titanium and superelastic material.

19. The assembly of claim 2 wherein the collar has a posterior surface perpendicular to a longitudinal axis of the transverse passageway.

20. The assembly of claim 4 wherein the collar has a height less than the height of the groove.

21. A method of attaching an orthopedic implant assembly to a bone of a patient, comprising
   a) positioning a stabilizing element against a surface of the patient's bone, the stabilizing element having an anterior surface, a posterior surface, and at least one bore, the bore having a first opening in the anterior surface, a second opening in the posterior surface smaller than the first opening, and a transverse passageway extending from the first opening to the second opening, and a biased stopping member within the bore and defining at least in part a reversibly expandable passageway having a smaller diameter configuration and a larger diameter configuration;
   b) providing a securing element having an elongated body, and a head at one end of the body and integral therewith, the head having a maximum diameter greater than the smaller diameter configuration of the passageway defined by the biased stopping member and greater than the second opening in the stabilizing element, so that the head is retained within the transverse passageway between the biased stopping member and the second opening in the stabilizing element;
   c) positioning the body of the securing element in the transverse passageway and posteriorly advancing the head of the securing element within the passageway defined by the biased stopping member and thereby displacing the biased stopping member to form the larger diameter configuration passageway defined thereby; and
   d) attaching the stabilizing element to the bone by advancing the head of the securing element posteriorly of the biased stopping member so that the passageway defined thereby returns to the smaller diameter configuration, to position the head within a posterior section of the transverse passageway between the biased stopping member and the second opening in the stabilizing element, and to position the body of the securing element within the patient's bone, so that the securing element is attached to the bone and is retained within the posterior section of the transverse passageway of the stabilizing element.

22. The method of claim 21 including, after the head of the securing element is positioned between the biased stopping member and the second opening in the stabilizing element, the step of longitudinally and angularly displacing the head of the securing element within the transverse passageway, so that the body of the securing element is positioned at an angle within the patient's bone relative to the surface of the bone.

23. An orthopedic implant assembly, comprising
   a) a stabilizing element having an anterior surface, a posterior surface, and at least one bore, the bore having a first opening in the anterior surface, a second opening in the posterior surface smaller than the first opening, and a transverse passageway extending from the first opening to the second opening, and a stopping member at an anterior section of the transverse passageway; and
   b) a securing element having an elongated body and a head secured to one end of the body, the head having a reversibly compressed configuration with a compressed diameter less than the diameter of the first opening and an uncompressed configuration with a diameter greater than a diameter of the stopping member and the second opening, so that the head of the securing element is retained within the transverse passageway between the stopping member and the second opening in the stabilizing element.

24. The assembly of claim 23 wherein the head of the securing element is configured to be displaceable posteriorly through the stopping member from an anterior to a posterior surface thereof.

25. The assembly of claim 23 wherein the head of the securing element has a plurality of slots and circumferentially disposed members, the circumferentially disposed members having posterior ends secured to the body of the securing element, and anterior ends radially moveable toward a longitudinal axis of the head of the securing element to form the compressed configuration and away from the longitudinal axis to form the uncompressed configuration.

26. The assembly of claim 23 wherein the stopping member is at the anterior end of the transverse passageway and defines the first opening in the stabilizing element.

27. The assembly of claim 23 wherein the stopping member has a posterior surface perpendicular to a longitudinal axis of the transverse passageway.

28. A method of attaching an orthopedic implant assembly to a bone of a patient, comprising
   a) positioning a stabilizing element against a surface of the patient's bone, the stabilizing element having an anterior surface, a posterior surface, and at least one bore, the bore having a first opening in the anterior surface, a second opening in the posterior surface smaller than the first opening, and a transverse passageway extending from the first opening to the second opening, and a stopping member at an anterior section of the transverse passageway;
   b) providing a securing element having an elongated body and a head secured to one end of the body, the head having a reversibly compressed configuration with a compressed diameter less than a diameter of the first opening and an uncompressed configuration with a diameter greater than the diameter of the stopping member and the second opening, so that the head of the securing element is retained within the transverse passageway between the stopping member and the second opening in the stabilizing element;

c) positioning the body of the securing element in the transverse passageway and posteriorly advancing the head of the securing element within a passageway defined by the stopping member and thereby compressing the diameter of the head of the securing element; and d) attaching the stabilizing element to the bone by advancing the head of the securing element posteriorly of the stopping member so that the diameter of the head of the securing element returns to the uncompressed configuration, to position the head within a posterior section of the transverse passageway between the stopping member and the second opening in the stabilizing element and the body of the securing element within the patient's bone, so that the securing element is attached to the bone and is retained within the posterior section of the transverse passageway of the stabilizing element.

* * * * *